United States Patent [19]

Christensen

[11] Patent Number: 5,487,916
[45] Date of Patent: Jan. 30, 1996

[54] METHOD FOR COATING PARTICLES IN A SPRAY-DRYING PLANT

[76] Inventor: Børge H. Christensen, Odinshøjvej 116, 3140 Ålsgarde, Denmark

[21] Appl. No.: 244,547

[22] PCT Filed: Dec. 17, 1992

[86] PCT No.: PCT/DK92/00384

§ 371 Date: Jul. 14, 1994

§ 102(e) Date: Jul. 14, 1994

[87] PCT Pub. No.: WO93/11844

PCT Pub. Date: Jun. 24, 1993

[30] Foreign Application Priority Data

Dec. 17, 1991 [DK] Denmark ................... 2017/91

[51] Int. Cl.$^6$ ................................. B05D 7/00
[52] U.S. Cl. .................. 427/213; 427/421; 118/303; 118/DIG. 5; 241/5; 241/39; 426/577
[58] Field of Search ................... 427/213, 421; 241/39, 5; 118/DIG. 5, 303; 426/577; 239/290

[56] References Cited

U.S. PATENT DOCUMENTS

| | | | |
|---|---|---|---|
| 3,615,723 | 10/1971 | Meade | 426/453 |
| 4,042,653 | 8/1977 | Beyn | 264/7 |
| 5,075,138 | 12/1991 | Tanaka et al. | 427/213 |
| 5,096,744 | 3/1992 | Takei et al. | 427/213 |
| 5,100,509 | 3/1992 | Pisecky et al. | 159/4.2 |

FOREIGN PATENT DOCUMENTS

| | | |
|---|---|---|
| 0378498 | 7/1990 | European Pat. Off. . |
| 0406903 | 1/1991 | European Pat. Off. . |
| 0423701 | 4/1991 | European Pat. Off. . |

*Primary Examiner*—Shrive Beck
*Assistant Examiner*—David M. Maiorana
*Attorney, Agent, or Firm*—Fish & Richardson

[57] ABSTRACT

A free-flowing powder of coated particles is produced by means of a spray dying plant using a hot drying gas or a spray cooling plant using cold drying gas. A coating composition in liquid form is supplied to the atomizing means of the plant, and the liquid coating composition is atomized into a flow of liquid droplets, which are allowed to collide with particles of a carrier material dispersed in a transport gas. The direction and rate of flow of the transport gas are adapted to prevent contact between the drying gas and the droplets, so that the liquid coating composition, before any substantial drying thereof, will form a continuous liquid coating layer on the particles. The thus applied continuous coating layer on the particles is then allowed to at least partially dry by contact with the drying gas before withdrawal of the coated particles from the spray-drying chamber of the plant to a moving bed in the form of loose agglomerates. Suitable coating compositions are fat-containing emulsions containing proteins.

18 Claims, 4 Drawing Sheets

METHOD FOR COATING PARTICLES IN A SPRAY-DRYING PLANT

FIELD OF THE INVENTION

The present invention relates to a method for coating particles in a spray-drying plant.

Coating of powder particles is desirable for many different reasons. Thus, e.g., coating may protect particles against humidity or oxidation. In connection with particles which are to be ingested, release of components from the particles during passage of the particles through the gastrointestinal system can be controlled by coating, e.g., in such a manner that the components in question are not released until after passage of the stomach. Coating of particles may also be a way of obtaining a slower release of active substances from the particles. Coating may cover an undesired taste, colour or texture of the particles. Furthermore, the coating may act as a protection against light and gasses.

As will be explained in the following, coating may also improve the possibility of spray-drying solutions or dispersions which are otherwise difficult or impossible to spray-dry, because the coating process may be utilized to expose the solutions or dispersions in a thin layer with a large surface, thus greatly enhancing evaporation.

Coating of powder particles may improve the handling of mixtures of powder products in which the individual components are to take part in a reaction which is initiated by decomposition of the coating.

BACKGROUND OF THE INVENTION

A known technique for coating powder particles comprises the use of a fluid bed plant. By means of this type of equipment, the powder particles are fluidized in air, the coating composition is atomized over the fluidized powder particles, and the coated particles are dried by continued passage in the fluid bed plant.

This type of fluid bed treatment is suitable only when coating powder particles have a size which is several times larger than the droplets of the atomized coating composition. When the particles are only a few times larger than the droplet size or smaller, an agglomeration occurs which results in the particles gluing together in clusters with large interstices of air, which is normally an undesired effect in a coating process.

In another technique, which is especially adapted for coating of relatively heavy particles in a fluid bed plant, a spray nozzle is placed at the bottom of a vertical tube in the center of fluidized powder particles and atomizes the coating composition upwards through the tube and concurrent with the powder particles, which particles are carried upwards through the same tube by means of an air flow. When the powder particles are coated, they are carried upwards, are dried, fall down into the fluidized powder particles and into the tube, and are coated with a new layer of the coating composition. This process is continued until the desired thickness of the coating layer has been obtained.

One problem associated with these two methods is that it is normally only possible to apply a very thin layer of a coating composition in each application stage. If a thicker layer of coating substance is applied at one time, the powder particles will tend to agglomerate due to sticky surfaces.

One known technique for coating of particles is to disperse powder particles in a liquid coating composition and spray-drying this mixed dispersion. However, in many cases, it is not realistic or at least not optimal to use this technique, in particular where the dispersion of the particles in the liquid coating composition will increase the viscosity to such an extent that spray atomisation of the dispersion becomes difficult or even impossible.

U.S. Pat. No. 3,615,723 describes a spray-drying process wherein the droplets, which are still tacky, are discharged at a screen where a mat is formed and dried. At least portions of the mat are subdivided into a particulate form (fines) and recirculated to the spray-drying chamber. The recirculated fines are added through a pipe discharging in a certain distance from the atomization zone. The dried, but still tacky droplets are discharged at the said screen in order to obtain an agglomeration of the particles. No coating is carried out by this process, and the dust particles are often over-heated due to lack of evaporation from the surfaces.

In U.S. Pat. No. 3,919,096, it is attempted to solve this problem by dispersing the particles in a liquid which is neutral to the particles and which is thereupon spray dried from the central channel of a special nozzle with three channel systems. The coating agent is sprayed from the outer channel system and the compressed air for atomizing both components is added through the intermediate channel.

U.S. Pat. No. 3,615,723 discloses recirculation, in connection with spray drying, of the smallest particles (dust) of already dried material to the spray drying chamber. The addition is performed through a tube the outlet of which is remote from the nozzle. The purpose of this process is an agglomeration of the dust with partially dried drops to obtain a uniform agglomerate size in the end product.

DK published Patent Application No. 160809 discloses agglomeration of substances in connection with spray drying, the fines (the non-agglomerated particles) being recycled to the central part of the atomization zone. The fines are dispersed in a minor part of the drying air, and the position for introducing the fine particles is controlled in such a manner that the average distance from the spraying wheel to the region in which the fine particles encounter the atomized droplets or partially dried particles is controlled. It is mentioned that formation of unwanted coated particles may take place when having a very short distance between the atomization wheel and the place for addition of powder particles.

EP patent application publication No. 344 375 discloses a spray-drying method and equipment for concurrent particle coating. The method is an application of a liquid substance, e.g. lecithin or other non-oxidative substance to particles which are derived from a mixture of solid particles and liquid by means of the spray-drying equipment.

EP patent application no. 423 701 A2 describes a method for granulation and coating by means of an equipment which uses drying air streams to effectuate granulating, coating and drying. The method comprises a supplying of an article to be coated and a supplying of a coating material, which supplyings are provided in such positions that the article to be coated and the coating material collide with each other before the article to be coated and the coating material are dispersed by the drying air streams. Cold air is supplied into a region where the article to be coated and the coated material collide with each other and hot air is supplied to a region spaced farther apart from the nozzles for supplying the article to be coated and the coating material than the region of the cold air supply.

SUMMARY OF THE INVENTION

As mentioned above, the present invention relates to a method for coating particles in a spray drying or spray cooling plant. In the present context, coating of particles means a coating of the total surface of the particles with a liquid coating composition. The dry matter composition of the coating composition may be equal to or different from the composition of the particles.

The method according to the invention for producing a free-flowing powder comprising particles of a carrier material coated with a coating composition using a spray-drying plant comprising a spray-drying chamber and an atomizing means arranged in the spray-drying chamber comprises supplying the coating composition in liquid form to the atomizing means of the plant and atomizing the liquid coating composition into a flow of droplets, supplying a flow of transport gas comprising particles of the carrier material dispersed therein to the spray-drying chamber separately from the coating composition, supplying a flow of drying gas to the chamber, the drying gas being of a temperature which will tend to solidify the liquid coating composition, allowing droplets in the flow of liquid droplets of the coating composition to collide with the particles of the carrier material dispersed in the transport gas, the direction and rate of flow of the transport gas being adapted to substantially prevent contact between on one hand the drying gas and on the other hand the droplets, so that the liquid coating composition, before any substantial drying thereof, will form a substantially continuous liquid coating layer on the particles, then allowing the thus applied continuous coating layer on the particles to at least partially dry by contact with the drying gas, and withdrawing the coated particles from the spray-drying chamber.

DETAILED DESCRIPTION OF THE INVENTION

Figure 1:
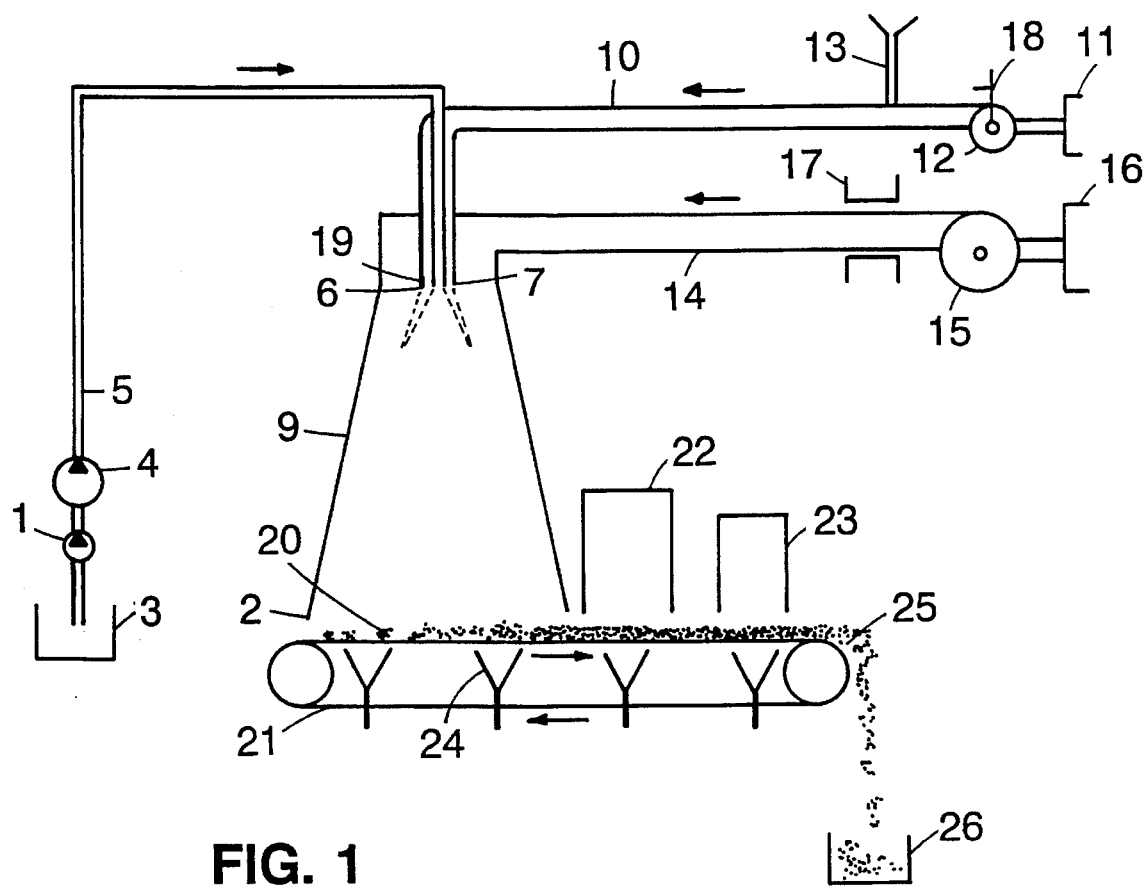
FIG. 1 diagrammatically illustrates a spray drying plant according to the instant invention.

It is a characteristic feature of most aspects of the method of the invention that on the one hand the flow of the transport gas with the particles of the carrier material dispersed therein and on the other hand the flow of the drying gas are directed substantially parallel to each other and are regulated so that they form a substantially distinct interface of a substantially constant shape in a region upstream of and adjacent to the region where the collision between the liquid droplets and the particles takes place, and normally, the flow of the transport gas with the carrier particles dispersed therein and the flow of the drying gas are regulated so that the substantially distinct interface of a substantially constant shape prevails also in the region where the collision between the liquid droplets and the particles takes place and in some cases also downstream of the region where the collision between the liquid droplets and the particles takes place.

The distinct interface of substantially constant shape (in this context, "constant" means constant over time; there may be variations in e.g. cross section shape or dimensions along the path from inlet formation of the interface and downstream) may be assessed by any suitable means, e.g., simply visually.

The flow of the drying gas and the flow of the transport gas are normally regulated so that they are both substantially laminar until the particles have been coated with the coating composition.

In particular suitable embodiments, the flow of the transport gas with the carrier particles dispersed therein is conducted in a substantially annular cross-sectional shape around the atomizing means, such as illustrated in the drawings and discussed in greater detail in the following. In particular, the flow of the transport gas with the carrier particles dispersed therein is conducted in a substantially circular cross-sectional shape around the atomizing means, the atomizing means being arranged substantially centrally in the circle.

While the method of the invention may be performed in such a manner that the particles will be substantially dry while air-borne in the spray drying chamber, in which case they can be removed from the spray drying chamber by, e.g., suction and be carried to a cyclone, an important embodiment of the method is one wherein only partial solidification of the substantially continuous coating layer in the spray-drying or spray-cooling chamber is performed, so that the particles with the partially solidified coating will be moderately sticky so that they will tend to form loose agglomerates when contacting each other, and the moderately sticky particles are collected on a bed of an air-penetrable material in the form of loose agglomerates and are further dried on the bed to substantially completely dry the coating layer on the agglomerated particles. Such a bed of air-penetrable material may be a moving bed of a filter cloth, such as in a "Filtermat" plant as described in the following.

It will be understood that the spray drying contemplated herein may be both a drying by evaporation and a drying by solidification of a molten coating composition by cooling. Thus, the drying gas is either a gas which has a temperature above the temperature of the transport gas, thus substantially drying the coating composition by supplying heat thereto, or a gas which has such a temperature below the temperature of the transport gas that it will result in solidification of the coating composition by cooling.

As will be discussed in greater detail in the following, an important feature of the present invention is that it can be effectively used for coating carrier particles which are of a material which is soluble or swellable in water.

The discoveries leading to the present invention were arrived at in connection with a thorough investigation of the coating process carried out with a model system consisting of an intensely red coating agent and an almost white powder. By this method, the quality of the coating could be followed directly through microscopy of the final products.

The investigations were concentrated around coating in connection with spray drying. The white powder to be coated consisted of pectin fibres, which swell so quickly upon contact with water that dispersing it in the coating agent was impossible. The coating agent consisted of a red-coloured protein solution, droplets of which are known to shell-dry extremely rapidly.

The investigations showed that even with a small amount of coating composition relative to the powder, a complete coating could be obtained, i.e., no visible white particles could be detected in the red final product prepared according to the invention.

It is believed that the coating composition through its high velocity away from the spraying device displaces a large part of the air molecules in an annular region around the device. Thereby, when the measure according to the present invention are not observed, a vacuum is created which sucks in the drying air. Through the collisions between the coating droplets and the molecules of the drying air, a gradual deceleration of the former takes place with a simultaneous filling of the vacuum. The energy exchange between the hot drying air and the droplets is very intensive in this phase, which results in an almost explosive emission of water molecules from the surface of the droplets. Thereby, the ability of the droplets to spread out on the particle surface quickly becomes diminished which is particularly apparent in operations where a thin layer of coating agent is to be spread over all particles.

The method of the invention solves this problem. It is believed that the powder, dispersed in air, is introduced into the innermost part of the above-mentioned vacuum region, so that the collisions between particles and droplets takes place in an annular region so close around the spraying device that the drying air has not, or only to a small extent, penetrated. Thereby, the dispersion is involved in the atomization process itself, in that the coating agent is flung away from the spraying device in the form of a film which, i.a., through the collisions with gas, such as air, molecules and particles of the dispersion, is split up into fine droplets.

The gas, such as air, used for dispersing the powder should be controlled both with respect to amount and temperature. The amount should be so small that the above-mentioned vacuum region is not filled out. If this happens, white particles will immediately appear in the final product. The temperature should be so low that the properties of the droplets with respect to coating do not deteriorate appreciably.

Controlling that there will not be supplied so much of the powder/air dispersion that the vacuum region is filled is easy in model systems, but in practice, there will generally not be such a colour difference between the powder and the coating agent that it can be used in optimising the coating process.

In the method of the invention, however, the introduction of the dispersion occurs in such a manner that the particles and the droplets form the above-mentioned characteristic flow pattern as long as there is a vacuum in the annular collision region. The part of the flow pattern taken up by the particles are shaped as a sharply defined cylinder, whereas the path taken up by the droplets are shaped like a cone in the case of nozzle spraying and like a disc in the case of centrifugal spraying. The transition between the cylinder and cone/disc is likewise sharply defined. If the supply of dispersion is pushed too high, this transition region starts to become fuzzy and dusty, and in the model system, one will find white particles in the otherwise red product as an indication of incomplete coating.

In coating operations where the coating agent is transferred from a liquid to a solid state through spray cooling, the same principles apply with respect to control of the powder-to-air ratio and of the ratio between the powder dispersion and the coating agent as applies when coating by means of spray drying. On the other hand, the temperature of the air used for dispersing the powder should in this case be so warm that the coating agent does not begin to solidify in the collision region.

Naturally, complete coating requires that there is a sufficient amount of coating agent available to cover the total particle surface. If this is not the case, a small deficiency of coating agent results in a mixture of coated and agglomerated particles, whereas with a larger deficiency of coating agent, a purely agglomerated product is obtained.

The method of the invention has thus proved also to be an effective production method for agglomerated products consisting of partly powdery and partly liquid starting materials.

A particular use of the invention has turned out to be very advantageous in connection with products which can not be spray dried in a normal manner because, when in a hot, dried condition, they exist in an amorphous plastic form that sticks to surfaces everywhere in the drying plant. The plastic form may be caused by the product temperature at the end of the drying process simply being higher than the melting point of the product, or by the crystallization proceeding too slowly compared to the time during which the droplets are freely suspended in the spray tower. Such products must normally be freeze dried or vacuum dried, since the product temperature may then be kept very low, and the drying time is very long.

By using freeze or vacuum dried powder at the beginning of the spray drying and coating it with the product, it is in many instances possible to reduce sticking to an acceptable level. Part of the obtained product is recycled back into the process and used according to the method of the invention as the powder to be coated.

With very difficult products, it may be necessary to recycle a very high proportion of the powder produced, e.g., 80%. Thereby it is achieved that the powder exits from the annular collision region as solid particles which are coated with a thin layer of liquid product and which therefore more easily than corresponding droplets are converted into non-sticky particles.

Thus, a very important embodiment is where the composition of the carrier particles is the same or substantially the same as the composition of the coating composition, and wherein the initial carrier particles are particles which have been made by other methods than spray drying, such as by freeze drying or vacuum drying or crystallisation. In this embodiment, part of the resulting coated product is recycled back into the process and is used as the carrier particles to be coated. The proportion of the coated particles produced which is recycled may, e.g., be at least 50%, such as about 80%, or it may go up to even 200–300% for certain productions, e.g. drying of sugar solutions which are difficult to crystallize in conventional processes, such as glucose or fructose solutions. By this method of the invention, full drying of the sugar may be obtained, resulting in little or no residual molasses.

The supply of an even flow of particles to the collision region may be brought about in different ways depending on whether the coating is to be carried out on spray plants having atomizing wheels or having nozzles.

The supply is most easily solved in spray plants with atomizing wheels, since a preferred embodiment of the supply means consists of a jacket around the conical or cylindrical atomizer housing in suitable distance therefrom, so that the flow of particles dispersed in air is able to pass in the resulting interspace. In a preferred embodiment, the particles are blown tangentially in at the top of the interspace, and the particles will therefore move downward along helical paths to the annular exit opening immediately above the annular collision region.

In the preferred embodiment, the tangential inlet is placed in such a manner that the particle flow at the outlet rotates in the opposite direction of the atomizing wheel. In this preferred embodiment, partly a completely uniform supply to the entire annular collision region and partly a maximum relative velocity between particles and droplets at the moment of collision is obtained.

As mentioned above, the advantage of this invention is that evaporation of the coating material by means of the hot air is prevented before the collision between the article to be coated and the coating material.

In comparison with the above-mentioned prior art the presently claimed method of producing a coated particle product involves a number of significant advantages. These advantages include the following:

commercially available spray-drying plants can be used, the present invention comprises a continuous process which compared to traditional coating methods gives lower production expenses, the method of the present invention has the advantage on the one hand that the flow of the transport gas with the particles of the carrier material dispersed therein and on the other hand the flow of the drying gas are directed substantially parallel to each other and are regulated so that they form a substantially distinct interface of a substantially constant shape in a region upstream of and adjacent to and also prevails in the region where the collision between the liquid droplets and the particles takes place. When comparing with the known art, e.g. EP 423701, the present invention, in a simple and efficient manner, provides the separation between the coating composition and the droplets of coating composition by regulation of the airflows, which is an efficient and flexible regulation resulting in a much more efficient and controlled process and total flexibility with respect to the use of conventional spray drying plants, the present invention makes it possible to coat particles which are water-soluble and have irregular shapes.

A special embodiment of the method of the invention can be characterized as a method for coating powder particles in a spray drying or spray cooling plant with a liquid coating agent, said method comprising dispersing the particles uniformly in an air flow with controlled ratio between powder and air, conducting the dispersion of powder and air into contact with the coating agent at the innermost part of the annular vacuum region formed through the movement of the coating agent droplets away from the atomizing means and to which region the drying or cooling air is prevented from penetrating, controlling the amount of the dispersion of powder in air supplied per unit of time in such a manner that it is at any time smaller than the amount required to fill the annular vacuum region, the control of the ratio between the amount of the dispersion of powder in air and the coating agent being exerted on the basis of visual or instrument recording or the characteristic flow pattern formed by the powder particles immediately prior to and subsequent to the collision with the coating agent droplets, and controlling the temperature of the dispersing air flow independent of the drying or cooling air so as to delay the initial transition of the liquid coating agent into solid form till after the collision with the powder particles.

Figure 3:
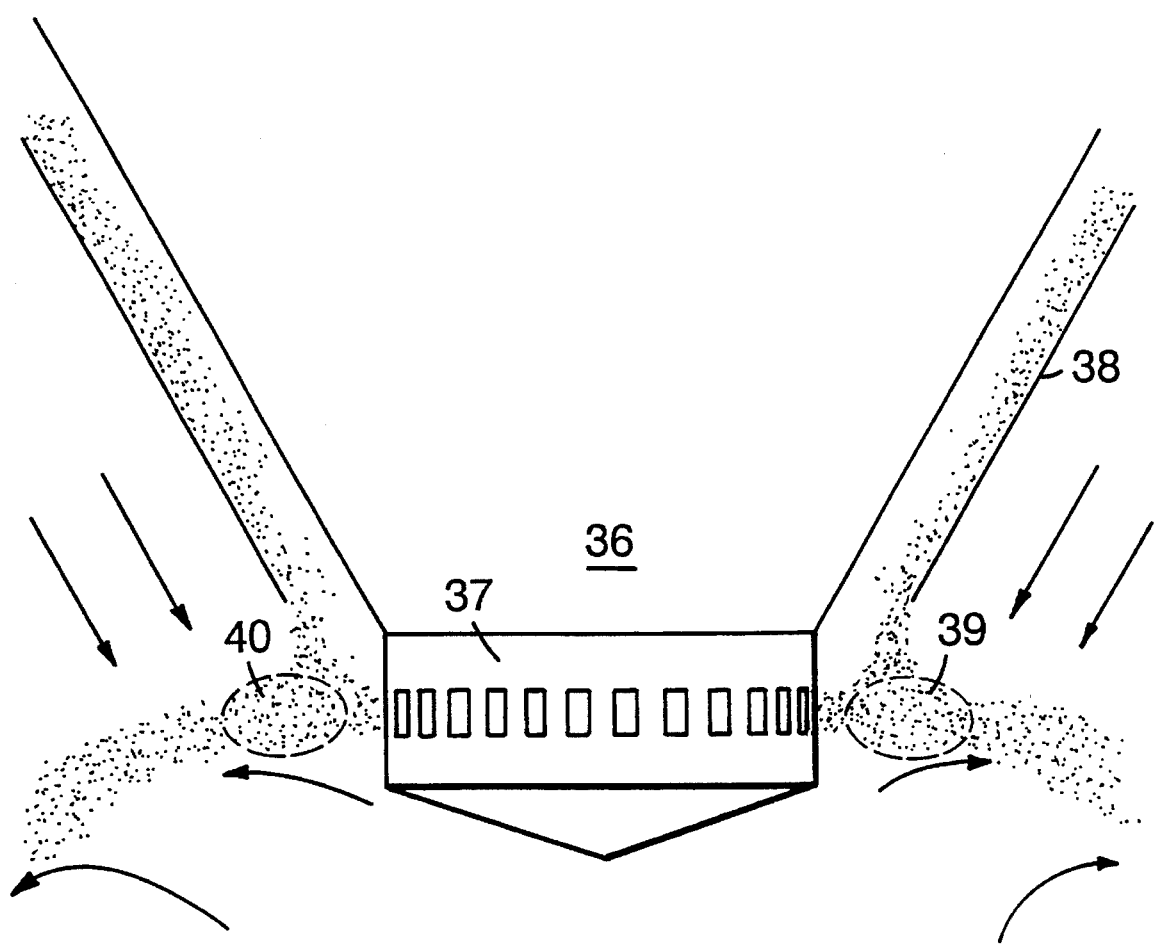
FIG. 3 shows a further embodiment of the instant invention.

FIG. 3 shows coating in connection with a spray plant having a conical atomizer housing 36 and an atomizing wheel 37. A jacket 38 is placed at a distance from the atomizing wheel, which ensures a suitable air and particle velocity in the interspace between the atomizer housing and the jacket. Reference numerals 39 and 40 designate the annular collision region.

In plants with nozzle atomization, which normally have several nozzles, the supply means to the individual nozzle consists in the preferred embodiment of a double walled tube where the nozzle and its feed tube are placed at the center, and where the particles are blown in tangentially into the interspace between the walls at the end opposite the nozzle.

Figure 2:
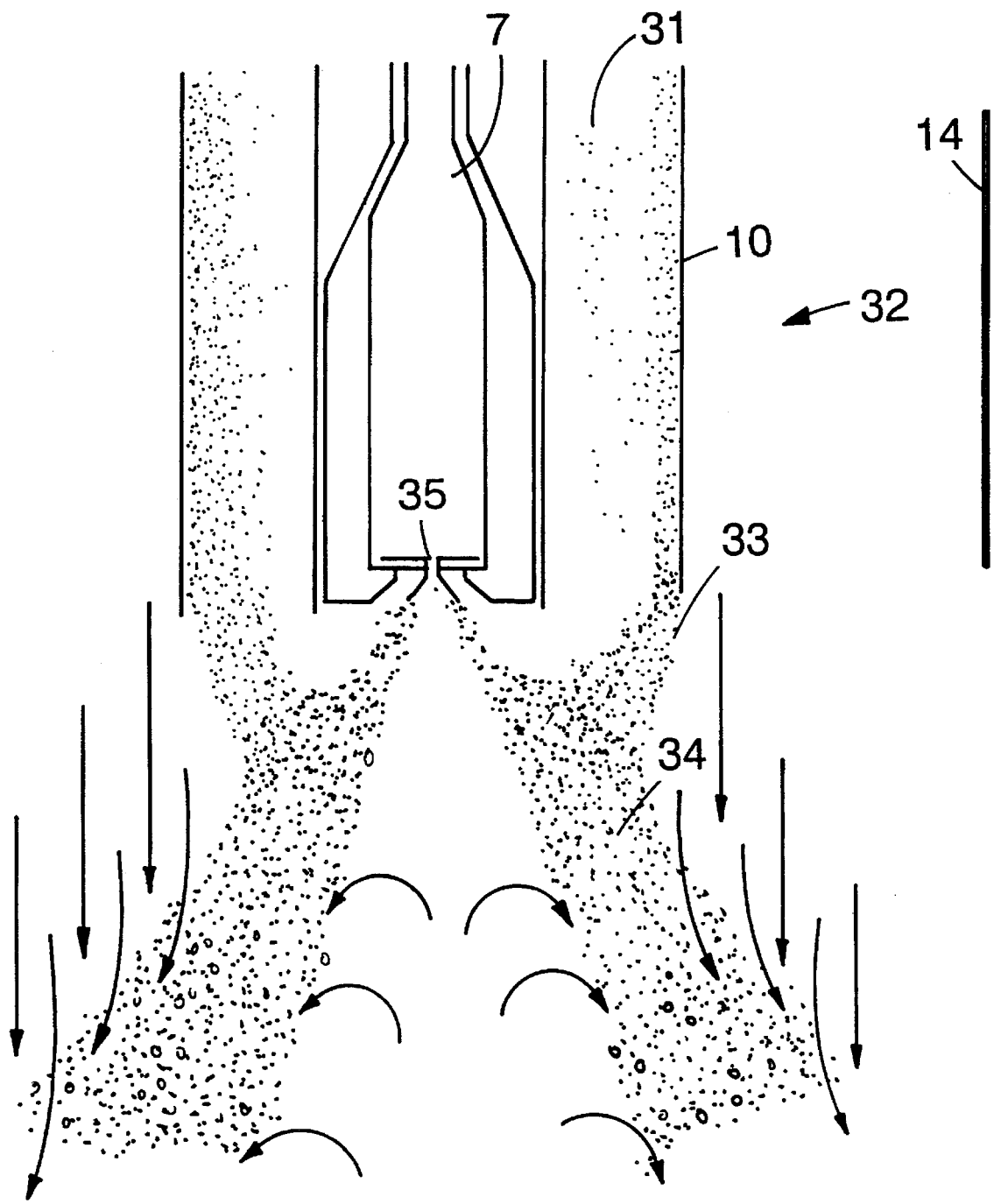
FIG. 2 illustrates the coating process of the instant invention.

FIG. 2 shows coating in connection with a spray plant with nozzle atomization. A nozzle 7 with a perforated disc 35 atomizes the coating agent so that the droplets move away from the disc 35 in paths describing a hollow cone. A double walled tube defines an interspace 31 conducting the particle flow to the annular collision region 34.

In the event of several nozzles, however, this means that the adjusted flow of particles to the spray plant must be divided into a number of equal partial flows to each respective nozzle. In a preferred embodiment, this is done by supplying the adjusted total particle flow into the center of a centrifugal ventilator which has as many exits as there are nozzles. By giving the exits completely identical shapes, it is ensured that the partial flows of particles to the individual nozzles will be exactly the same.

Figure 4A:
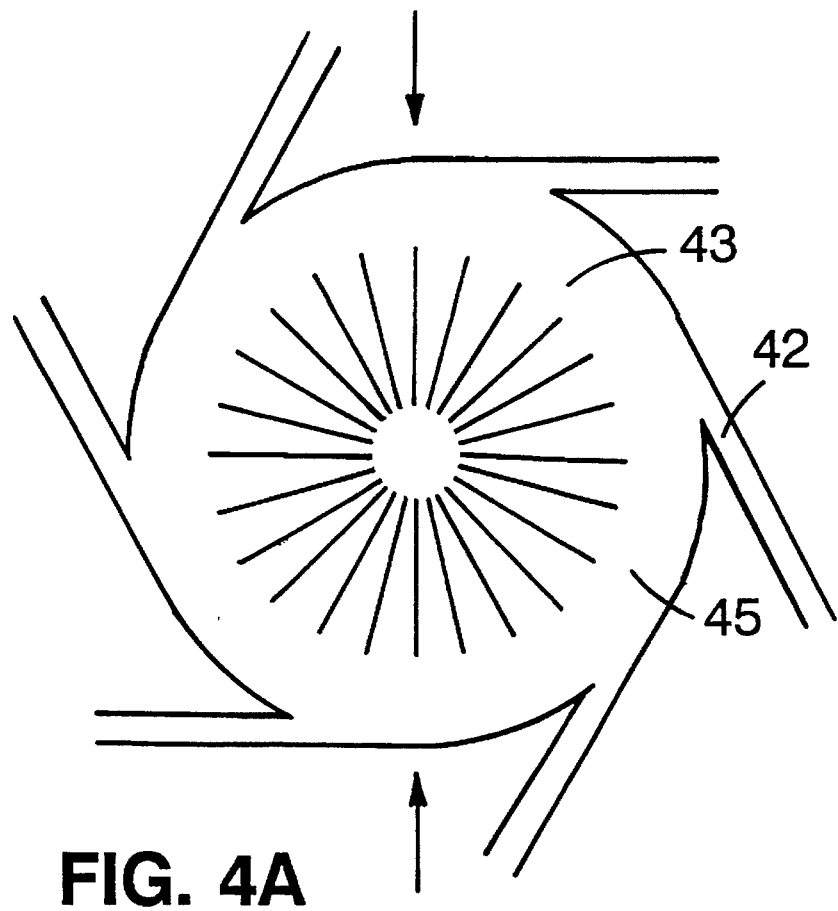
FIG. 4A shows the top view of a centrifugal ventilator.
Figure 4B:
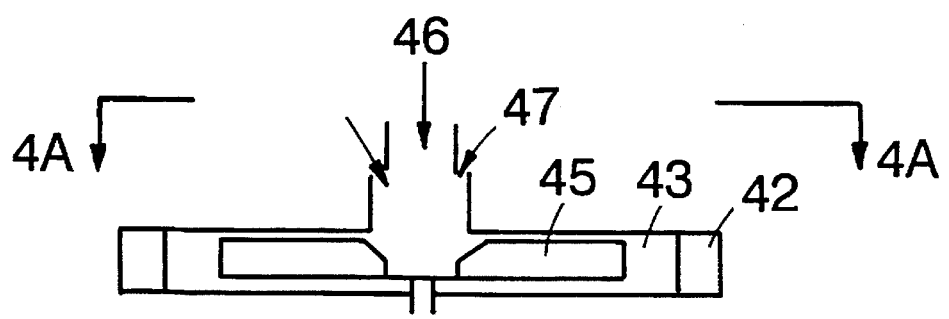
FIG. 4B shows the cross-section of the centrifugal ventilator through a line a—a of FIG. 4A.

FIGS. 4A and 4B are somewhat diagrammatic top plan and side views, respectively, of a centrifugal ventilator with 6 exits for dividing a flow of powder into 6 partial flows. Reference numeral 43 designates a ventilator housing, and reference numeral 42 designates one of six identical exits which are arranged in a rotation-symmetrical manner. Reference numeral 45 designates the ventilator wheel, reference numeral 46 designates the central inlet for the powder flow, and reference numeral 47 designates the inlet for the transport air.

FIG. 1 diagrammatically illustrates what may be considered as a conventional spray-drying or spray-cooling plant. This kind of spray-drying or spray-cooling plant may preferably be used when carrying out the method according to the invention. The spray-drying or spray-cooling plant comprises a spray-drying or spray-cooling chamber 9 wherein a carrier material is coated with a coating composition. The spray-drying or spray-cooling plant illustrated in FIG. 1 is provided with nozzle means for dispensing a coating composition in a liquid form, however, a spray-drying or spray-cooling plant having an atomizing wheel for dispensing the coating composition in a liquid form could also be used. The spray-drying or spray-cooling plant in FIG. 1 could be provided with a number of nozzles, such as 1–20, but to simplify the description the spray-drying or spray-cooling plant in FIG. 1 is only provided with one nozzle.

A coating composition in liquid form is introduced into the spray-drying or spray-cooling chamber 9 through a high-pressure atomizing nozzle 7 (positioned in the upper part, preferably 6–8 m, more preferably 7 m above the bottom of the of the spray-drying or spray-cooling chamber 9) atomizing the liquid coating composition into droplets. The high-pressure atomizing nozzle 7 is fed with the liquid coating composition under pressure via a supply pipe 5. The pressure is generated by a high-pressure feed pump 4 fed by a feeding pump 1 and communicating with a storage 3 containing the liquid coating composition. The spray-drying or spray-cooling chamber 9 has the form of a hollow frustum of a pyramid, with an opening 2 in the bottom, this opening 2 is preferably of 2 by 2 m and an upper almost circular opening 8, preferably having an inner diameter in the order of 1.2 m. The high-pressure feed pump 4 (such as a Rannie) generating a pressure in the range of 150–250 atm, preferably in the order of 200 atm. The feeding pump 1, preferably generating a pressure in the range of 2–3 atm. The supply pipe 5 is a high-pressure pipe, preferably with an inner diameter in the order of 8 mm. The length of the vertical part of the supply pipe 5 above the spray-drying and spray-cooling chamber 9 is preferably in the order of 1.3 m.

The particles of the carrier material, to which the droplets of liquid coating composition is applied, are supplied with a flow of a transport gas, preferably air, to the spray-drying or spray-cooling chamber 9 from an inlet 19 communicating with a particle transporting pipe 10. The particles of the carrier material are dispensed from a pipe 13, preferably having an inner diameter in the order of 12 cm into the particle-transporting pipe 10 and air-borne by the flow of transport gas to the inlet 19. The flow of the transport gas is derived by a fan 12 from the atmosphere through an inlet air filter 11.

After coating of the particles in the spray-drying or spray-cooling chamber 9, the air-borne coated particles are brought into contact with a drying or cooling gas, preferably air, in order to solidify the coating at least partly. The drying or cooling air is through a grid 6 supplied from a supply pipe 14 communicating with a fan 15 deriving air from the atmosphere through an inlet air filter 16. The grid provides a minor decrease in the pressure: in the drying or cooling air and give a more laminar flow of the drying or cooling air into the spray-drying or spray-cooling chamber 9. Depending on the actual process to be carried out by the spray-drying or spray-cooling plant, the supply pipe 14 may be provided with air-heating means, such as a gas burner from Maxon, or air-cooling means 17, respectively.

The direction and the rate of flow of the transport gas are adapted by means of a regulator 18, preferably a slide, regulating the flow through the fan 12. This adaptation substantially prevents contact between, on the one hand, the drying gas and, on the other hand, the droplets so that the liquid coating composition, before any substantial drying thereof, will form a substantially continuous-liquid coating layer on the particles.

Alternatively or additionally, the supply of drying— or cooling-gas may be adjusted by regulators not shown in the drawings.

The particles with at least partly solidified coating in the spray-drying or spray-cooling chamber 9 will be moderately sticky so that they will tend to form loose agglomerates 20 when contacting each other. The agglomerates 20 will be transported through the opening 2 and collected on a movable filtermat belt 21 of air-penetrable material in the form of loose agglomerates. The velocity of the filtermat belt 21 is preferably adjustable. The agglomerates 20 are transported by the belt 21 into at least one drying chamber 22 performing a further second drying of the agglomerates 20 and preferably into a cooling chamber 23 for cooling of the agglomerates 20 before leaving the movable filtermat belt 21. The finished agglomerates 20 are transported to a point 25 where the belt returns, the agglomerate here fall into a hopper 26 for optional further processing. The belt may preferably having a length of 8–14 m, and preferably a width of 1.5–2.0 m, more preferably in the order of 1.8 m.

Under the movable filtermat belt 21 in positions under the spray-drying or spray-cooling chamber 9, the chamber 22 and the chamber 23, respectively, exhaust means 24, such as adjustable exhausting fans are provided. The exhaust means 24 draw the drying or cooling air from the spray-drying or spray-cooling chamber 9 through the mat of the product and the air-penetrable material. The air-penetrable material is preferably of polyester or polypropylene and is preferably of a kind of fabric having small loops in its outer weaver and bigger loops in its inner weaver so as to prevent material from getting stocked in the fabric.

The high-pressure atomizing nozzle 7 used in the spray-drying and spray-cooling plant illustrated in FIG. 1 is preferably a Whirl chamber nozzle from Delavan providing a mist having a hollow cone shape.

The movable filtermat belt 21, the drying chamber 22, the cooling chamber 23, the exhaust means 24 and fans 12 and 15 may preferably be parts from a F500 or F5000 NIRO Filtermat plant.

FIG. 2 illustrates the zone around a high-pressure atomizing nozzle 7 operating in a spray-drying or spray-cooling plant as described in FIG. 1. In this zone, on the one hand, a flow of a transport gas 31 with particles of a carrier material dispersed therein (supplied from a particle-transporting pipe 10) and, on the other hand, a flow of the drying or cooling gas 32 (supplied from a supply pipe 14) are directed substantially parallel to each other and are regulated so that they form a substantially distinct interface of a substantially constant shape in a region 33 upstream of and adjacent to a region 34 in which the collision between the dispensed liquid droplets and the particles takes place. The droplets are dispensed from the high-pressure atomizing nozzle 7 having a disc 35 with a central opening wherefrom the droplets are dispensed in a hollow conical mist.

1 feeding pump
2 opening
3 storage
4 high-pressure feed pump
5 supply pipe
6 grid
7 high-pressure atomizing nozzle
8 opening
9 spray-drying or spray-cooling chamber
10 particle-transporting pipe
11 inlet air filter
12 fan
13 pipe
14 supply pipe
15 fan
16 inlet air filter
17 air-heating means or air-cooling means
18 regulator
19 inlet
20 agglomerate
21 movable filtermat belt
22 drying chamber
23 cooling chamber
24 exhaust means
25 point
26 hopper
31 transport gas
32 drying- or cooling-gas
33 region
34 region
35 opening

EXAMPLE

Preparation of a fat- and protein-coated pectin product useful as feed additive for weaning piglets This example illustrates the utilization of the method of the invention for the preparation of pectin particles coated with an fat- and protein-containing emulsion.

Pectin swells in water, resulting in an aqueous phase of a high viscosity, and could therefore not be coated by conventional immersion in an emulsion of the type in question.

As the coating composition, an emulsion having the following composition was prepared:

| Whey concentrate, 33 wt % dry matter | 100 kg |
|---|---|
| Blood concentrate, 33 wt % dry matter | 100 kg |
| Pork lard | 27 kg |
| Fish oil | 7 kg |
| Total | 234 kg |

The blood concentrate was obtained by increasing the dry matter content of porcine whole blood from 16–17 wt. % to 33 wt. % dry matter content in a vacuum evaporator.

The whey concentrate, the blood concentrate, the pork lard and the fish oil were mixed at a temperature of 40° C. to 42° C. to obtain an emulsion, which was homogenized in two steps at a pressure of 120 bar in the first step and 30 bar in the second step to reduce the size of the fat globules in the emulsion to a diameter of less than 2 μm.

The resulting emulsion was fed to the nozzle of a spray-drying equipment of the type illustrated in FIG. 1 ("Filtermat F500" from Damrow with an evaporation capacity of 500 lbs/hour, spray nozzle type Delavan working at a pressure of 150 bar and giving an open hollow cone spray).

A pectin powder was prepared from the following ingredients:

| Ingredients | wt %, dry matter | wt %, limits |
|---|---|---|
| pectin from dried potato pulp | 20 | 5–25 |
| pectin from dried apple pulp | 54 | 15–60 |
| pectin from dehydrated citrus pulp | 5 | 5–25 |
| Guar gum | 10 | 5–25 |
| Plantago psyllium or Semen psyllii | 10 | 5–25 |
| Betainhydrochloride | 1 | 1–2 |

The pectin powder particles have an average size of 50 μm (in the ranges of 10 μm to 100 μm).

25 kg of the above-mentioned pectin powder was added to the Filtermat F500 as a dispersion in air and was coated with the obtained emulsion in the Filtermat F500 spray-drying equipment.

The Filtermat F500 consisted of the following components:

- a spray-drying tower with a square bottom of 2 by 2 m, the distance from the spray nozzle to the conveyor belt being 7 m,
- an application pipe for the particles of the carrier material having a diameter of 12 cm and a length of 1.30 m,
- the application pipe was in the center equipped with an internal pipe having an internal diameter of 8 mm which internal pipe ended in the nozzle,
- a Filtermat belt with a width of 1.80 m and a total length of 11 m, the part of the belt which collected the coated powders was 5 m. The Filtermat belt which comprises an air-penetrable filter cloth made of a woven 2-layer polymeric material and woven in a way so that the air-penetrating pores of the upper layer have a smaller diameter than the pores of the bottom layer,
- a retention chamber over the Filtermat belt next to the spray tower,
- a secondary drying chamber next to the retention chamber and a cooling chamber at the outlet end of the belt, The drying air in the spray tower had an inlet temperature of 250° C. and an outlet temperature of 75° C. When discharged from the spray tower the coated particles were further dried at the retention chamber and of the drying chamber of the filter bed by means of air having an inlet temperature of 75° C. and an outlet temperature of 60° C. The dried and coated particles were further cooled at ambient temperature.

A coated, agglomerated pectin-containing product having a particle size of 50 μm and comprising 20 wt. % pectin powder was obtained.

In the following, some examples of some parameters of the method are given:

The liquid coating material is dispersed into the air flow at a pressure in the range of 0 to 400 bar, preferably in the range of 1 to 300 bar, more preferably in the range of 10 to 200 bar and most preferably in the range of 25 to 150 bar.

The weight ratio between the air and the particles of the carrier material may be in the range of 1:99 to 99:1, preferably in the range of 5:95 to 95:5, more preferably in the range of 20:80 to 80:20, even more preferably in the range of 30:70 to 70:30 and most preferably in the range of 40:60 to 60:40, such as 50:50.

The weight ratio between the amount of the dispersed particles of the carrier material and the coating composition may be in the range of 1:99 to 50:50, preferably in the range of 5:95 to 40:60, more preferably in the range of 10:90 to 30:70, most preferably in the range of 15:85 to 25:75, such as 20:80.

The particles of the carrier are substantially soluble and swellable in water and have irregular shapes with an average diameter in the range of 0.1 to 100 μm, preferably in the range of 1 to 80 μm, more preferably in the range of 10 to 60 μm and most preferably in the range of 25 to 50 μm.

The particles of the carrier may substantially be selected from a group consisting of vegetables, cereals, seeds, fruits, spices, food additives, bacterial cultures, metals, polymeric fibres, alkaline substances, acid substances and a mixture thereof or from a group consisting of proteins, carbohydrates, fats, vitamins, minerals and a mixture thereof.

The coating composition may be homogenized in two steps before the spray-drying or spray-cooling process by means of a homogenizer at a pressure which in the first step is in the range of 50 to 200 bar, preferably in the range of 75 to 150 bar, more preferably in the range of 100 to 125 bar, such as 120 bar and a pressure in the second step which is in the range of 10 to 75 bar, preferably in the range of 20 to 60 bar and most preferably in the range of 30 to 50 bar, such as 40 bar.

The coating composition is atomized at the nozzle at a pressure in the range of 250 to 50 bar, preferably in the range of 200 to 100 bar and more preferably in the range of 125 to 160 bar, such as 150 bar.

In this context spray-drying is carried out using drying air in the spray-drying chamber with an inlet temperature in the range of 400° C. to 100° C., preferably in the range of 350° C. to 150° C., more preferably in the range of 300° C. to 200° C. The outlet temperature of the air from the spray-drying chamber is in the range of 150° C. to 25° C., preferably in the range of 125° C. to 50° C., more preferably in the range of 110° C. to 60° C. and most preferably in the range of 100° C. to 75° C.

When spray-cooling, the temperature has to be below the solidification point of the coating material and the air used for cooling may substantially have a temperature in the range of minus 25° C. to plus 25° C., preferably in the range of 0° C. to 20° C., more preferably in the range of 10° C. to 15° C. Ambient temperatures can be used.

The coated powders may be further dried at a conveyor belt, preferably of the Filtermat type using air with an inlet temperature in the range of 90° C. to 40° C., preferably in the range of 85° C. to 50° C. and more preferably in the range of 75° C. to 60° C. and an outlet temperature being in the range of 75° C. to 30° C., preferably in the range of 65° C. to 40° C. and more preferably-in the range of 60° C. to 50° C.

The dried, coated powders can eventually be cooled at temperatures in the range of 5° C. to 25° C., preferably in the range of 10° C. to 20° C. More often the ambient temperature is used.

I claim:

1. A method for producing a free-flowing powder comprising particles of a carrier material coated with a coating composition using a spray-drying plant comprising a spray-drying chamber and an atomizing means selected from a high-pressure atomizing nozzle and an atomizing wheel arranged in the spray-drying chamber, the method comprising supplying the coating composition in liquid form to the atomizing means of the plant and atomizing the liquid coating composition into a flow of droplets, supplying a flow of transport gas comprising particles of the carrier material dispersed therein to the spray-drying chamber separately from the coating composition, supplying a flow of drying gas to the chamber, the drying gas being of a temperature selected to solidify the liquid coating composition, allowing droplets in the flow of liquid droplets of the coating composition to collide with the particles of the carrier material dispersed in the transport gas, the direction and flow rate of the transport gas being adapted to substantially prevent contact between the drying gas and the droplets, so that the liquid coating composition, before any substantial drying thereof, will form a substantially continuous liquid coating layer on the particles, the flow of the transport gas with the particles of the carrier material dispersed therein and the flow of the drying gas being directed substantially parallel to each other and being regulated so that they form a substantially distinct interface of a substantially constant shape in a region upstream of and adjacent to the region where the collision between the liquid droplets and the particles takes place, then allowing the thus applied continuous coating layer on the particles to at least partially dry by contact with the drying gas, and withdrawing the coated particles from the spray-drying chamber.

2. A method according to claim 1, wherein the flow of the transport gas with the carrier particles dispersed therein and the flow of the drying gas are regulated so that the substantially distinct interface of a substantially constant shape prevails also in the region where the collision between the liquid droplets and the particles takes place.

3. A method according to claim 2 wherein the flow of the transport gas with the carrier particles dispersed therein and the flow of the drying gas are regulated so that the substantially distinct interface of a substantially constant shape prevails also downstream of the region where the collision between the liquid droplets and the particles takes place.

4. A method according to claim 1, wherein the flow of the drying gas and the flow of the transport gas are substantially laminar until the particles have been coated with the coating composition.

5. A method according to claim 1, wherein the flow of the transport gas with the carrier particles dispersed therein is conducted in a substantially annular cross-sectional shape around the atomizing means.

6. A method according to claim 5, wherein the flow of the transport gas with the carrier particles dispersed therein is conducted in a substantially circular cross-sectional shape around the atomizing means, the atomizing means being arranged substantially centrally in the circle.

7. A method according to claim 1, wherein only partial solidification of the substantially continuous coating layer in the spray-drying or spray-cooling chamber is performed, so that the particles with the partially solidified coating will be moderately sticky so that they will tend to form loose agglomerates when contacting each other, and the moderately sticky particles are collected on a bed of an air-penetrable material in the form of loose agglomerates and are further dried on the bed to substantially completely dry the coating layer on the agglomerated particles.

8. A method according to claim 7, wherein the bed of air-penetrable material is a moving bed of a filter cloth.

9. A method according to claim 1, wherein the drying gas is either a gas which has a temperature above the temperature of the transport gas, thus substantially drying the coating composition by supplying heat thereto, or a gas which has such a temperature below the temperature of the transport gas that it will result in solidification of the coating composition by cooling.

10. A method according to claim 1, wherein the carrier particles are particles of a material which is soluble or swellable in water.

11. A method according to claim 1, wherein the composition of the carrier particles is the same or substantially the same as the composition of the coating composition.

12. A method according to claim 11, wherein the initial carrier particles are particles which have been made by other methods than spray drying, such as by freeze drying or vacuum drying.

13. A method according to claim 11 or 12, wherein part of the resulting coated product is recycled back into the process and are used as the carrier particles to be coated.

14. A method according to claim 13, wherein the proportion of the coated particles produced which is recycled is at least 50%.

15. A method according to claim 14, in which the proportion of the coated particles produced which is recycled is about 80%.

16. A method according to claim 1, wherein the carrier particles are pectin particles.

17. A method according to claim 1 or 16, wherein the coating composition is a fat-containing emulsion.

18. A method according to claim 17, wherein the fat-containing emulsion also contains proteins.

* * * * *